United States Patent
Miyachi

(10) Patent No.: US 11,006,837 B2
(45) Date of Patent: May 18, 2021

(54) PHOTOACOUSTIC IMAGE GENERATION APPARATUS

(71) Applicant: FUJIFILM Corporation, Tokyo (JP)

(72) Inventor: Yukiya Miyachi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1091 days.

(21) Appl. No.: 15/468,447

(22) Filed: Mar. 24, 2017

(65) Prior Publication Data

US 2017/0196462 A1 Jul. 13, 2017

Related U.S. Application Data

(63) Continuation of application No. PCT/JP2015/004863, filed on Sep. 24, 2015.

(30) Foreign Application Priority Data

Sep. 29, 2014 (JP) .............................. JP2014-198885

(51) Int. Cl.
*A61B 5/00* (2006.01)
*A61B 8/13* (2006.01)
(Continued)

(52) U.S. Cl.
CPC ............ *A61B 5/0095* (2013.01); *A61B 5/742* (2013.01); *A61B 6/469* (2013.01); *A61B 8/13* (2013.01);
(Continued)

(58) Field of Classification Search
None
See application file for complete search history.

(56) References Cited

U.S. PATENT DOCUMENTS 6,221,016 B1 4/2001 Hayakawa
2010/0174197 A1 7/2010 Nakajima et al.
(Continued)

FOREIGN PATENT DOCUMENTS

EP   2638851 A1   9/2013
JP   2009-31262 A   2/2009
(Continued)

OTHER PUBLICATIONS

International Search Report for PCT/JP2015/004863 dated Jan. 26, 2016.
(Continued)

*Primary Examiner* — Joel F Brutus
(74) *Attorney, Agent, or Firm* — Birch, Stewart, Kolasch & Birch, LLP

(57) ABSTRACT

An insertion needle has a light guide member for guiding light emitted from a light source, a light emitting portion for emitting light guided by the light guide member, and a photoacoustic wave generating portion for generating photoacoustic waves caused by light emitted from the light emitting portion. A photoacoustic image generation unit generates a photoacoustic image based on the detection signal of the photoacoustic waves. A distal end candidate extraction unit extracts a distal end candidate region from the shallow side of the image based on the strength of the detection signal of the photoacoustic waves. An image output unit displays the extracted distal end candidate region on an image display unit.

17 Claims, 10 Drawing Sheets

(51) Int. Cl.
| | |
|---|---|
| *A61M 25/06* | (2006.01) |
| *G01N 29/24* | (2006.01) |
| *A61M 5/32* | (2006.01) |
| *A61B 6/00* | (2006.01) |
| *A61B 8/00* | (2006.01) |
| *A61B 17/34* | (2006.01) |
| *G16H 40/63* | (2018.01) |
| *G01N 29/06* | (2006.01) |
| *G16H 30/20* | (2018.01) |
| *G01S 7/52* | (2006.01) |
| *A61B 18/14* | (2006.01) |
| *A61B 90/00* | (2016.01) |
| *A61B 10/04* | (2006.01) |
| *G01N 21/17* | (2006.01) |
| *A61B 10/02* | (2006.01) |
| *A61B 5/06* | (2006.01) |

(52) U.S. Cl.
CPC .............. *A61B 8/461* (2013.01); *A61B 8/469* (2013.01); *A61B 17/3403* (2013.01); *A61M 5/32* (2013.01); *A61M 25/06* (2013.01); *G01N 29/0609* (2013.01); *G01N 29/2418* (2013.01); *G16H 30/20* (2018.01); *G16H 40/63* (2018.01); *A61B 5/061* (2013.01); *A61B 5/6848* (2013.01); *A61B 10/02* (2013.01); *A61B 10/0283* (2013.01); *A61B 2010/045* (2013.01); *A61B 2017/3413* (2013.01); *A61B 2018/1425* (2013.01); *A61B 2090/373* (2016.02); *A61B 2090/3929* (2016.02); *G01N 21/1702* (2013.01); *G01N 2201/08* (2013.01); *G01S 7/52073* (2013.01)

(56) References Cited

U.S. PATENT DOCUMENTS

| | | | |
|---|---|---|---|
| 2012/0078103 | A1* | 3/2012 | Tashiro ................ A61B 8/5207 600/443 |
| 2013/0237802 | A1* | 9/2013 | Irisawa ................ A61B 5/0095 600/407 |
| 2014/0051966 | A1* | 2/2014 | Irisawa .................... A61B 1/07 600/407 |
| 2014/0155739 | A1 | 6/2014 | Manohar |
| 2015/0297092 | A1 | 10/2015 | Irisawa |
| 2016/0270667 | A1 | 9/2016 | Nakajima et al. |

FOREIGN PATENT DOCUMENTS

| | | |
|---|---|---|
| JP | 2012-70837 A | 4/2012 |
| JP | 2012-120747 A | 6/2012 |
| JP | 2013-13713 A | 1/2013 |
| JP | 2014-155596 A | 8/2014 |
| WO | WO 2014/109148 A1 | 7/2014 |

OTHER PUBLICATIONS

Written Opinion of the International Searching Authority for PCT/JP2015/004863 dated Jan. 26, 2016.
Extended European Search Report for European Application No. 15846581.5, dated Oct. 13, 2017.

* cited by examiner

PHOTOACOUSTIC IMAGE GENERATION APPARATUS

CROSS REFERENCE TO RELATED APPLICATIONS

The present application is a Continuation of PCT International Application No. PCT/JP2015/004863 filed on Sep. 24, 2015, which claims priority under 35 U.S.C. § 119(a) to Japanese Patent Application No. 2014-198885 filed on Sep. 29, 2014. Each of the above applications is hereby expressly incorporated by reference, in its entirety, into the present application.

BACKGROUND OF THE INVENTION

1. Field of the Invention

The present invention relates to a photoacoustic image generation apparatus, more specifically, to a photoacoustic image generation apparatus for generating a photoacoustic image by detecting photoacoustic waves generated in a subject after emitting light to the subject.

2. Description of the Related Art

As a kind of image examination method capable of examining the state of the inside of a living body in a non-invasive manner, an ultrasound examination method is known. In ultrasound examination, an ultrasound probe capable of transmitting and receiving ultrasound waves is used. When ultrasound waves are transmitted to the subject (living body) from the ultrasound probe, the ultrasound waves propagate through the living body to be reflected on the tissue interface. By receiving the reflected ultrasound waves using the ultrasound probe and calculating the distance based on the time until the reflected ultrasound waves return to the ultrasound probe, it is possible to image the state of the inside.

In addition, photoacoustic imaging for imaging the inside of the living body using the photoacoustic effect is known. In general, in photoacoustic imaging, pulsed laser light, such as a laser pulse, is emitted into the body. In the living body, a living tissue absorbs the energy of the pulsed laser light, and ultrasound waves (photoacoustic waves) due to adiabatic expansion due to the energy are generated. By detecting the photoacoustic waves using an ultrasound probe or the like and forming a photoacoustic image based on the detection signal, it is possible to visualize the inside of the living body based on the photoacoustic waves.

For photoacoustic imaging, JP2009-31262A discloses a combination of photoacoustic imaging and treatment using an insertion needle. In JP2009-31262A, an affected part such as a tumor, a part suspected to be an affected part, or the like is found by generating a photoacoustic image and observing the image. In order to examine such a part more precisely or in order to perform injection into the affected part, sampling of cells, injection into the affected part, and the like are performed using an insertion needle, such as an injection needle or a cytodiagnosis needle. In JP2009-31262A, it is possible to perform insertion while observing the affected part using a photoacoustic image.

In addition, JP2013-13713A also discloses a combination of photoacoustic imaging and an insertion needle. In JP2013-13713A, the insertion needle has a light emitting portion. Light emitted from a laser light source is guided to the light emitting portion of the insertion needle using, for example, an optical fiber, and is emitted to the outside from the light emitting portion. By detecting photoacoustic waves, which are generated by absorbing the light emitted from the light emitting portion of the insertion needle, using an ultrasound probe and generating a photoacoustic image based on the detection signal, it is possible to check the position of the insertion needle.

Here, the success of the brachial plexus block is largely based on the localization of the nerve, the position of a needle, and an appropriate technique for local anesthetic injection. In recent years, nerve block injection is performed by inserting an insertion needle while observing an ultrasound image. However, there is a problem that it is difficult for the insertion needle to be visually recognized only with the ultrasound image. In the insertion, it is important that the entire needle can be seen. However, in order to prevent pneumothorax and the like, it is most important to check the position of the distal end of the needle. In photoacoustic imaging, usually, emission of light to the subject is performed from the surface of the subject. In particular, when the distal end of the insertion needle is inserted up to a deep position (for example, a position deeper than 3 cm from the subject surface), light emitted from the subject surface does not sufficiently reach the insertion needle that has been inserted to the deep position. Accordingly, it is difficult to check the position of the distal end of the insertion needle in a photoacoustic image.

To solve the problem, there is a technique disclosed in WO2014/109148A. In WO2014/109148A, light emitted from the light source is guided to the vicinity of the distal end of the insertion needle using an optical fiber or the like, and the light is emitted to a photoacoustic wave generating portion of the insertion needle from there. In this manner, it is possible to check the position using a photoacoustic image even when the insertion needle is inserted up to a deep position.

SUMMARY OF THE INVENTION

In WO2014/109148A, since the photoacoustic wave generating portion is provided at the distal end of the insertion needle, it is possible to generate photoacoustic waves at one point of the distal end of the insertion needle. However, the photoacoustic waves generated at the distal end of the insertion needle may be multi-reflected by the main body of the insertion needle and the bone, tissues, and the like, which are present around the main body of the insertion needle and have high reflectances of acoustic waves. Such multi-reflections cause artifacts in a photoacoustic image (sound artifacts). In addition, when the light emitted to the photoacoustic wave generating portion is emitted to blood vessels or the like present in the insertion direction of the insertion needle, photoacoustic waves are generated in the blood vessels or the like, and such photoacoustic waves also cause artifacts (light artifacts), These artifacts are obstacles to checking the position of the insertion needle using a photoacoustic image. The above problems also occur similarly in the case of checking the position of an insert other than the insertion needle.

In view of the above, it is an object of the present invention to provide a photoacoustic image generation apparatus capable of easily checking the position of an insert by suppressing the influence of artifacts.

In order to achieve the aforementioned object, the present invention provides a photoacoustic image generation apparatus comprising: an insert at least a part of which is inserted into a subject and which has a light guide member for guiding light emitted from a light source, a light emitting portion for emitting light guided by the light guide member, and a photoacoustic wave generating portion for generating photoacoustic waves caused by light emitted from the light emitting portion; acoustic wave detection means for detecting photoacoustic waves emitted from the insert; photoacoustic image generation means for generating a photoacoustic image based on a detection signal of the photoacoustic waves; distal end candidate extraction means for extracting a distal end candidate region from a shallow side based on a strength of the detection signal of the photoacoustic waves; and image output means for displaying the extracted distal end candidate region on image display means.

In the photoacoustic image generation apparatus of the present invention, it is preferable that the distal end candidate extraction means extracts a distal end candidate region with a predetermined number as an upper limit.

It is preferable that the photoacoustic image generation apparatus of the present invention further has correction means for suppressing a strength of a detection signal of photoacoustic waves in a distal end candidate region other than a distal end candidate region located in a shallowest portion, in a photoacoustic image, relative to a strength of a detection signal of photoacoustic waves in the distal end candidate region located in the shallowest portion.

With the distal end candidate region located in the shallowest portion among the extracted distal end candidate regions as a reference, the correction means may correct a strength of a detection signal of photoacoustic waves in each distal end candidate region using a coefficient according to a distance in a depth direction between each distal end candidate region and the reference distal end candidate region.

It is preferable that the correction means emphasizes the distal end candidate region located in the shallowest portion relative to remaining distal end candidate regions.

The distance may be defined as a distance in the depth direction between a center-of-gravity position of the reference distal end candidate region and each of remaining distal end candidate regions.

The coefficient is a maximum when the distance is 0, and a value of the coefficient decreases as the distance increases.

The distal end candidate extraction means may extract, as a distal end candidate region, a region where the strength of the detection signal of the photoacoustic waves is equal to or greater than a threshold value.

The distal end candidate extraction means may extract a distal end candidate region based not only on the strength of the detection signal of the photoacoustic waves but also on an area of a region where the strength of the detection signal of the photoacoustic waves is equal to or greater than a threshold value.

The image output means may mask a region other than the extracted distal end candidate region in the photoacoustic image.

It is preferable that the distal end candidate extraction means extracts the distal end candidate region after performing smoothing processing on the detection signal of the photoacoustic waves.

The insert may have an opening, and have an inner cavity thereinside.

The photoacoustic wave generating portion may include a light absorption member that absorbs the light emitted from the light emitting portion to generate photoacoustic waves.

The insert may be a needle inserted into a subject.

The light emitting portion may emit at least some of light beams guided by the light guide member toward an inner wall of the inner cavity.

The acoustic wave detection means may further detect reflected acoustic waves of acoustic waves transmitted toward a subject. In this case, the photoacoustic image generation apparatus of the present invention may further have reflected acoustic wave image generation means for generating a reflected acoustic wave image based on the reflected acoustic waves.

The image output means may display the extracted distal end candidate region on the image display means so as to be superimposed on the reflected acoustic wave image.

In the photoacoustic image generation apparatus of the present invention, it is easy to check the position of the insert by suppressing the influence of artifacts.

DESCRIPTION OF THE PREFERRED EMBODIMENTS

Figure 1:
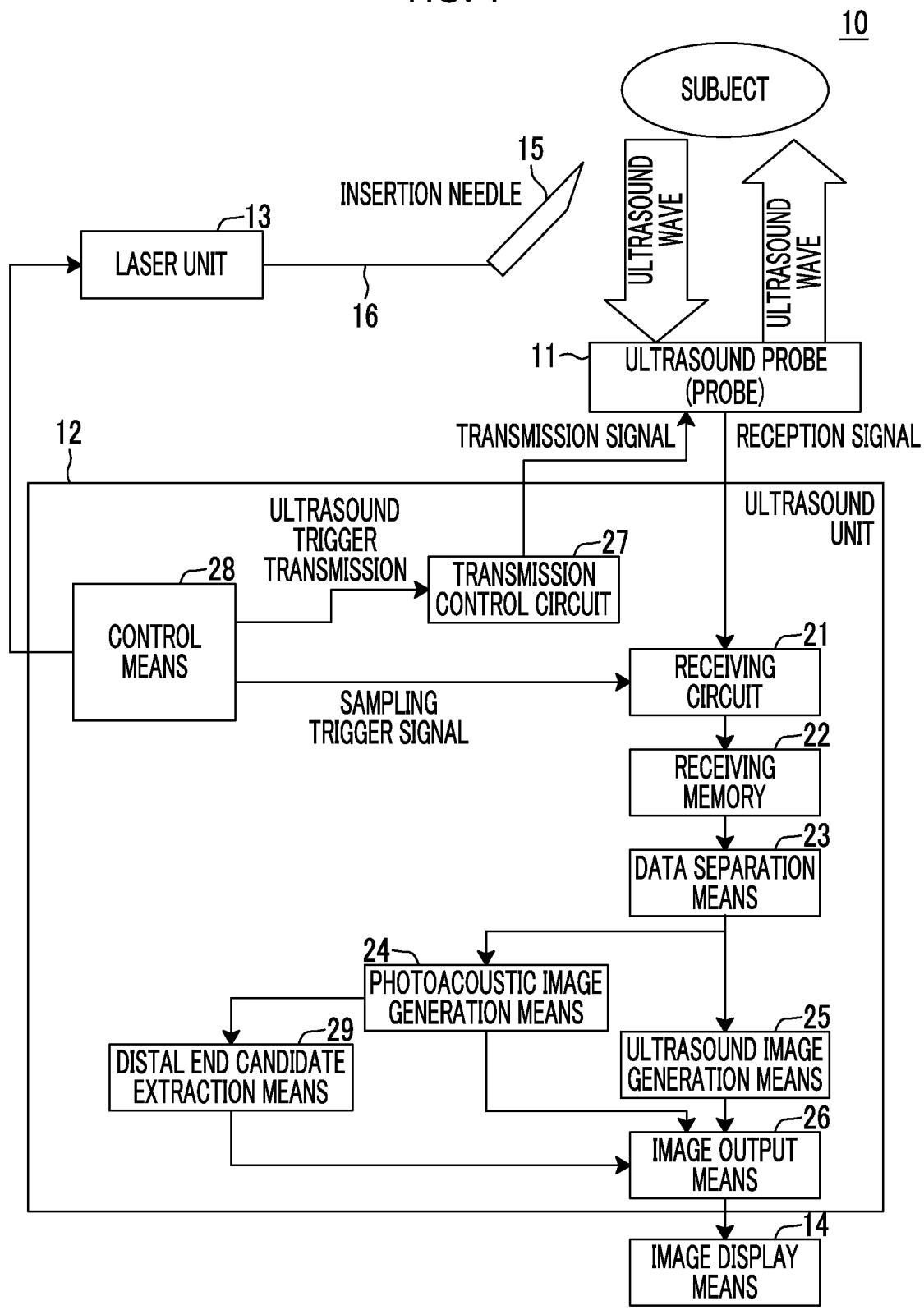
FIG. 1 is a block diagram showing a photoacoustic image generation apparatus according to a first embodiment of the present invention.

Hereinafter, embodiments of the present invention will be described in detail with reference to the diagrams. FIG. 1 shows a photoacoustic image generation apparatus according to a first embodiment of the present invention. A photoacoustic image generation apparatus 10 includes a probe (ultrasound probe) 11, an ultrasound unit 12, a laser unit 13, and an insertion needle 15. In the embodiment of the present invention, an ultrasound wave is used as an acoustic wave. However, the present invention is not limited to the ultrasound wave, and an acoustic wave having an audible frequency may be used as long as an appropriate frequency can be selected according to an examination target, measurement conditions, or the like.

The laser unit 13 is a light source. Light emitted from the laser unit 13 is guided to the insertion needle 15 that is an insert, for example, using light guide means, such as an optical fiber 16. The laser unit 13 is a laser diode light source (semiconductor laser light source), for example. Alternatively, the laser unit 13 may be a light amplification type laser light source having a laser diode light source as a seed light source. Types of light sources are not particularly limited, and the laser unit 13 may be a solid state laser light source using yttrium aluminum garnet (YAG), alexandrite, and the like. Light sources other than the laser light source may be used.

Figure 2:
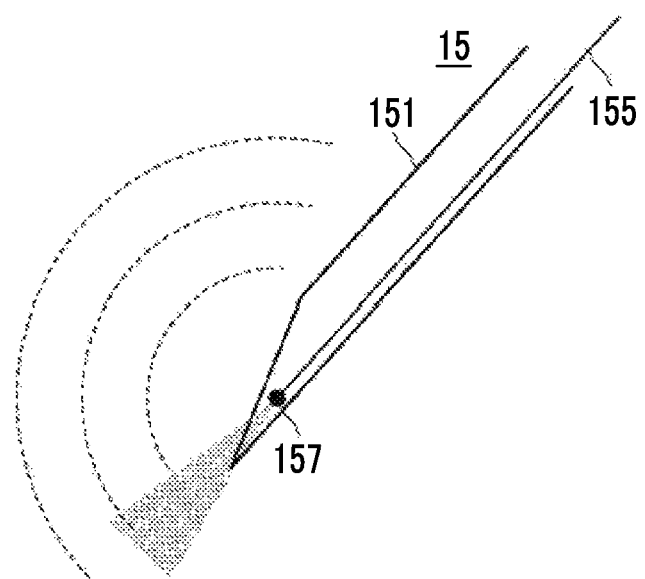
FIG. 2 is a cross-sectional view showing an insertion needle.

The insertion needle 15 is a needle inserted into the subject. FIG. 2 shows a cross section of the insertion needle 15. The insertion needle 15 includes: a hollow insertion needle body 151 that has an opening at the distal end formed at an acute angle and has an inner cavity thereinside; a light guide member 155 for guiding light emitted from the laser unit 13 to the vicinity of the opening of the insertion needle; and a light absorption member 157 that absorbs laser light emitted from the light guide member 155 to generate photoacoustic waves.

The light guide member 155 and the light absorption member 157 are disposed inside the insertion needle body 151. The light guide member 155 is connected to the optical fiber 16 (refer to FIG. 1) through an optical connector provided in a proximal end portion of the insertion needle 15, for example. The light guide member 155 is formed of, for example, an optical fiber, and the end surface of the optical fiber on the light traveling side when viewed from the laser unit 13 forms a light emitting portion. For example, laser light of 0.2 mJ is emitted from the light emitting portion. Instead of providing the optical connector, the optical fiber 16 may be inserted into the tube 158 and the optical fiber 16 itself may be used as the light guide member 155.

The light absorption member 157 is provided at a position to which the light emitted from the light emitting portion of the light guide member 155 is emitted. The light absorption member 157 is provided in the vicinity of the distal end of the insertion needle 15 and on the inner wall of the insertion needle body 151. The light absorption member 157 is a photoacoustic wave generating portion that absorbs the light emitted from the light emitting portion to generate photoacoustic waves. The light absorption member 157 is formed of, for example, an epoxy resin containing black pigment mixed thereinto, a polyurethane resin, a fluorine resin or silicone rubber, and black paint having high light absorptivity with respect to the wavelength of laser light. In FIG. 2, the light absorption member 157 is drawn larger than the light guide member 155. However, without being limited to this, the light absorption member 157 may have approximately the same size as the diameter of the light guide member 155.

The light absorption member 157 is not limited to that described above, and a metal film or an oxide film having light absorptivity with respect to the wavelength of laser light may be used as the light absorption member 157. For example, a film of an oxide, such as an iron oxide, a chromium oxide, and a manganese oxide having high light absorptivity with respect to the wavelength of laser light, can be used as the light absorption member 157. Alternatively, a metal film such as Ti or Pt which has lower light absorptivity than oxides and has high biocompatibility may be used as the light absorption member 157. The position where the light absorption member 157 is provided is not limited to the inner wall of the insertion needle body 151. For example, a metal film or an oxide film that is the light absorption member 157 may be formed on the light emitting surface of the light guide member 155 in a thickness of, for example, about 100 nm by vapor deposition or the like, and the metal film or the oxide film may cover the light emitting surface. In this case, at least some of light beams emitted from the light emitting surface of the light guide member 155 are absorbed by the metal film or the oxide film that covers the light emitting surface, and photoacoustic waves are generated from the metal film or the oxide film.

The "vicinity" of the distal end of the insertion needle 15 means a position where it is possible to generate photoacoustic waves capable of imaging the position of the distal end of the insertion needle 15 with accuracy, which is required for insertion work, in a case where the light emitting surface of the light guide member 155 and the light absorption member 157 are disposed at the position. For example, "vicinity" indicates the range of 0 mm to 3 mm toward the proximal end side from the distal end of the insertion needle 15. Also in subsequent embodiments, the meaning of the vicinity of the distal end is the same.

Referring back to FIG. 1, a probe 11 is acoustic wave detection means, and has a plurality of detector elements (ultrasound transducers) arranged in a one-dimensional manner. The probe 11 detects photoacoustic waves generated from the light absorption member 157 (refer to FIG. 2) after the insertion needle 15 is inserted into the subject. In addition to the detection of photoacoustic waves, the probe 11 performs transmission of acoustic waves (ultrasound waves) to the subject and reception of reflected acoustic waves (reflected ultrasound waves) of the transmitted ultrasound waves. In addition, transmission and reception of ultrasound waves may be performed at separate positions. For example, ultrasound waves may be transmitted from a position different from the probe 11, and reflected ultrasound waves of the transmitted ultrasound waves may be received by the probe 11. The probe 11 is not limited to the linear probe, but may be a convex probe or a sector probe.

The ultrasound unit 12 has a receiving circuit 21, a receiving memory 22, data separation means 23, photoacoustic image generation means 24, ultrasound image generation means 25, image output means 26, a transmission control circuit 27, control means 28, and distal end candidate extraction means 29. The ultrasound unit 12 forms a signal processing device.

The receiving circuit 21 receives a detection signal output from the probe 11, and stores the received detection signal in the receiving memory 22. Typically, the receiving circuit 21 includes a low noise amplifier, a variable gain amplifier, a low pass filter, and an analog to digital convertor (AD converter). The detection signal of the probe 11 is amplified by the low noise amplifier, and then the gain is adjusted according to the depth by the variable gain amplifier and a high-frequency component is cut by the low pass filter. Then, conversion into a digital signal is performed by the AD converter, and the digital signal is stored in the receiving memory 22. The receiving circuit 21 is formed by one integral circuit (IC), for example.

The probe 11 outputs a detection signal (also referred to as a photoacoustic signal) of photoacoustic waves and a detection signal (also referred to as a reflected ultrasound signal) of reflected ultrasound waves, and a photoacoustic signal and a reflected ultrasound signal (sampling data thereof) after AD conversion are stored in the receiving memory 22. The data separation means 23 reads the sampling data of the photoacoustic signal from the receiving memory 22, and transmits the sampling data to the photoacoustic image generation means 24. In addition, the data separation means 23 reads the sampling data of the reflected ultrasound signal from the receiving memory 22, and transmits the sampling data to the ultrasound image generation means (reflected acoustic wave image generation means) 25.

The photoacoustic image generation means 24 generates a photoacoustic image based on the photoacoustic signal detected by the probe 11. The generation of a photoacoustic image includes, for example, image reconstruction such as phase matching addition, detection, and logarithmic conversion. The ultrasound image generation means 25 generates an ultrasound image (reflected acoustic wave image) based on the reflected ultrasound signal detected by the probe 11. The generation of an ultrasound image also includes image reconstruction such as phase matching addition, detection, and logarithmic conversion.

The distal end candidate extraction means 29 extracts a distal end candidate region from the shallow side of the image based on the strength of the detection signal of photoacoustic waves. The strength of the detection signal of photoacoustic waves corresponds to a pixel value (gradation value) in a photoacoustic image. Therefore, the following explanation will be given on the assumption that the distal end candidate extraction means 29 extracts a distal end candidate region based on the pixel value of the photoacoustic image. The distal end candidate extraction means 29 extracts a distal end candidate region with a predetermined number as an upper limit, for example. In a photoacoustic image, the distal end of the insertion needle 15 is present in a portion with a high pixel value (portion where detected photoacoustic waves are strong). It is preferable that the distal end candidate extraction means 29 extracts, as a distal end candidate region, a region where the pixel value of the photoacoustic image is equal to or greater than a threshold value.

Here, a photoacoustic signal after reconstruction in photoacoustic image generation can be regarded as a photoacoustic image. The distal end candidate extraction means 29 may extract a distal end candidate region from any image (signal) in the image generation step. Specifically, a distal end candidate region may be extracted from the photoacoustic signal after reconstruction, or a distal end candidate region may be extracted from the photoacoustic signal after detection and logarithmic conversion. Alternatively, a distal end candidate region may be extracted from an image obtained by converting the photoacoustic signal after detection and logarithmic conversion into display gradation using a lookup table or the like. From the point of view of ease of processing, it is preferable that the photoacoustic signal after detection and logarithmic conversion is subject to the distal end candidate extraction processing.

The image output means 26 outputs the extracted distal end candidate region to image display means 14, such as a display device. At this time, it is preferable that the image output means 26 outputs the extracted distal end candidate region to the image display means 14 in a state in which the distal end candidate region is superimposed on the ultrasound image. The image output means 26 may output an image of a portion of the distal end candidate region extracted in the photoacoustic images to the image display means 14. In other words, the image output means 26 may mask a region other than the distal end candidate region extracted in the photoacoustic image.

The control means 28 controls each unit in the ultrasound unit 12. For example, in the case of acquiring a photoacoustic image, the control means 28 transmits a trigger signal to the laser unit 13 so that the laser unit 13 emits laser light. In addition, the control means 28 controls the sampling start timing of photoacoustic waves by transmitting a sampling trigger signal to the receiving circuit 21 in response to the emission of the laser light. The area where photoacoustic waves are to be detected may be divided into a plurality of areas. In this case, emission of light to the subject and detection of photoacoustic waves are performed for each area.

In the case of acquiring an ultrasound image, the control means 28 transmits an ultrasound wave transmission trigger signal for giving an instruction to transmit ultrasound waves to the transmission control circuit 27. When the ultrasound wave transmission trigger signal is received, the transmission control circuit 27 makes the probe 11 transmit ultrasound waves. The probe 11 detects reflected ultrasound waves by performing a scan while shifting the acoustic line by one line at a time, for example. The control means 28 transmits a sampling trigger signal to the receiving circuit 21 according to the timing of ultrasound wave transmission, thereby starting the sampling of reflected ultrasound waves.

Figure 3:
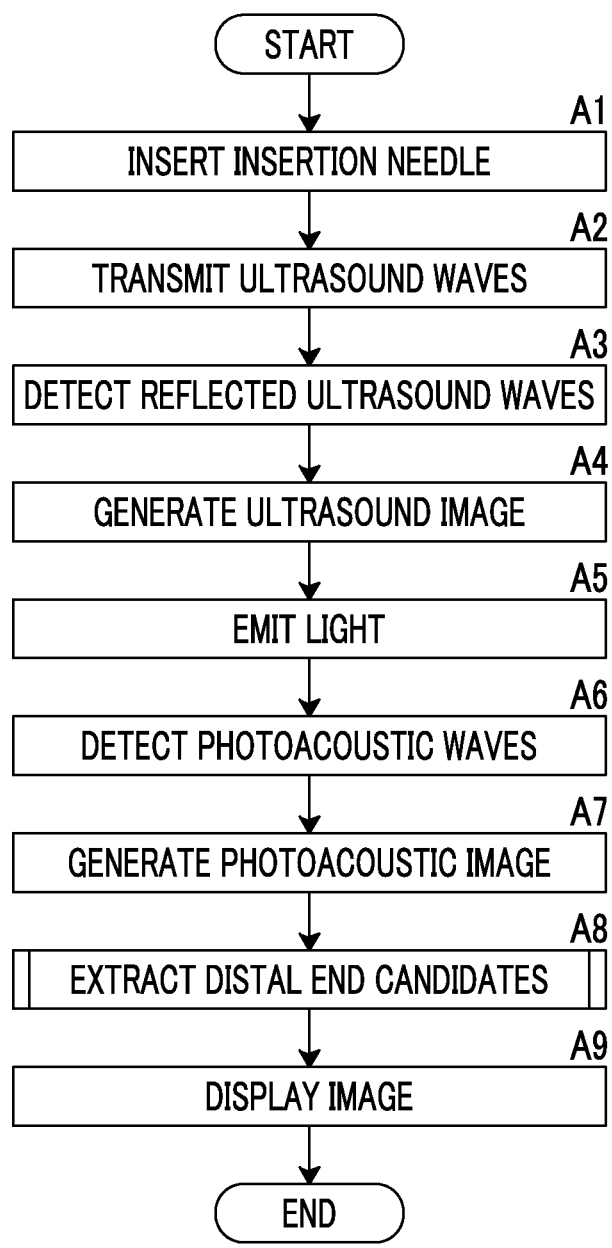
FIG. 3 is a flowchart showing an operation procedure.

FIG. 3 shows an operation procedure. A doctor or the like inserts the insertion needle 15 into the subject (step A1). After the insertion of the insertion needle 15, the control means 28 transmits an ultrasound trigger signal to the transmission control circuit 27. The transmission control circuit 27 makes the probe 11 transmit ultrasound waves in response to the ultrasound trigger signal (step A2). The probe 11 detects reflected ultrasound waves after the transmission of ultrasound waves (step A3). In addition, transmission and reception of ultrasound waves may be performed at separate positions. For example, ultrasound waves may be transmitted from a position different from the probe 11, and reflected ultrasound waves of the transmitted ultrasound waves may be received by the probe 11.

The reflected ultrasound signal output from the probe 11 is stored in the receiving memory 22 through the receiving circuit 21. The data separation means 23 transmits the reflected ultrasound signal stored in the receiving memory 22 to the ultrasound image generation means 25. The ultrasound image generation means 25 generates an ultrasound image based on the reflected ultrasound signal (step A4).

The control means 28 of the ultrasound unit 12 transmits a trigger signal to the laser unit 13. When the trigger signal is received, the laser unit 13 starts laser oscillation to emit pulsed laser light (step A5). The pulsed laser light emitted from the laser unit 13 is guided to the vicinity of the distal end of the insertion needle 15 by the light guide member 155 (refer to FIG. 2), and is emitted from the light absorption member 157.

The probe 11 detects photoacoustic waves generated in the subject due to the emission of the laser light (step A6). The receiving circuit 21 receives the photoacoustic signal from the probe 11, and stores the sampling data of the photoacoustic signal in the receiving memory 22. Here, photoacoustic waves propagate one way from the vicinity of the distal end of the insertion needle 15, which is a generation position of the photoacoustic waves, to the probe 11, while the reflected ultrasound waves transmitted from the probe 11 propagate back and forth between the probe 11 and the ultrasound wave reflection position. Accordingly, the detection of the reflected ultrasound waves requires twice the time for the detection of the photoacoustic waves generated at the same depth position. For this reason, the sampling clock of the AD converter at the time of reflected ultrasound wave sampling may be half at the time of photoacoustic wave sampling.

The data separation means 23 transmits the photoacoustic signal stored in the receiving memory 22 to the photoacoustic image generation means 24. The photoacoustic image generation means 24 generates a photoacoustic image based on the photoacoustic signal (step A7). The distal end candidate extraction means 29 extracts a region, which is a distal end candidate of the insertion needle 15, from the photoacoustic image (step A8). The image output means 26 displays, on the image display means 14, an image obtained by superimposing an image, which is obtained by masking a region other than the distal end candidate region extracted in step A8 in the photoacoustic image generated in step A7, on the ultrasound image generated in step A4 (step A9).

Figure 4:
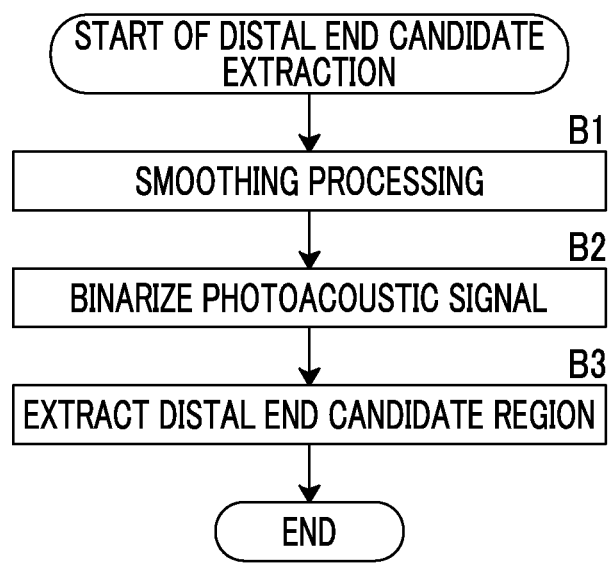
FIG. 4 is a flowchart showing the procedure of distal end candidate extraction processing.

FIG. 4 shows the procedure of the distal end candidate extraction process. Here, explanation will be given on the assumption that a distal end candidate region is extracted based on the photoacoustic signal after detection and logarithmic conversion. The distal end candidate extraction means 29 performs smoothing processing on the photoacoustic signal (photoacoustic image) after detection and logarithmic conversion (step B1). As the smoothing processing, for example, filter processing using a Gaussian filter can be used. It is preferable that the filter size of the Gaussian filter is smaller than the size of the distal end portion of the insertion needle 15.

The distal end candidate extraction means 29 binarizes a photoacoustic signal after the smoothing processing (step B2). By the binarization, the photoacoustic signal is divided into a portion where the signal strength is equal to or greater than a threshold value and a portion where the signal strength is less than the threshold value. After the binarization, a region where pixels are continuous is extracted as a distal end candidate region (step B3). At this time, the distal end candidate extraction means 29 may extract a region where pixels are continuous by a predetermined number from the shallow side. When a distal end candidate region is extracted from the shallow side and the number of extracted distal end candidate regions reaches a predetermined number, the extraction of distal end candidate regions are ended. When the number of regions where pixels are continuous is less than the predetermined number, the region extraction may be ended at that point in time.

Figure 5A:
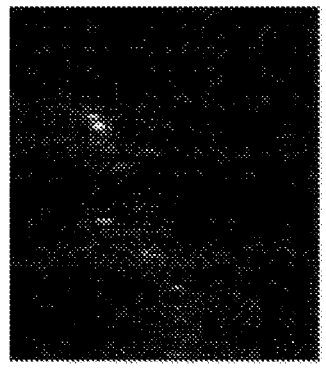
FIG. 5A is a diagram showing a photoacoustic signal after detection and logarithmic conversion as an image.
Figure 5B:
FIG. 5B is a diagram showing an image subjected to smoothing processing.
Figure 5C:
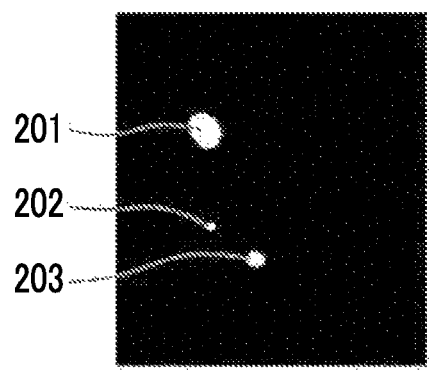
FIG. 5C is a diagram showing a binary image.
Figure 5D:
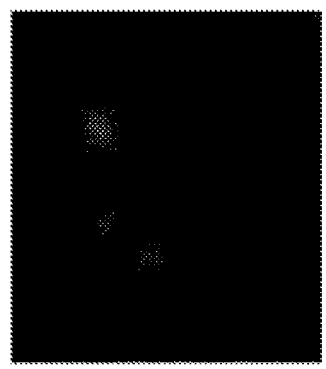
FIG. 5D is a diagram showing an image of an extracted distal end candidate region.

FIG. 5A shows a photoacoustic signal after detection and logarithmic conversion as an image, and FIG. 5B is an image obtained by performing smoothing processing on the image. FIG. 5C is a binary image, and FIG. 5D is an image of an extracted distal end candidate region. In these images, an upper portion of the paper corresponds to the shallow side of the subject, and the depth increases downward.

In FIG. 5A, a portion where the detected photoacoustic signal is the strongest, that is, a portion where the pixel value of the photoacoustic image is the largest corresponds to a position where the light absorption member 157 (refer to FIG. 2) is present in the insertion needle 15. Although it is ideal that photoacoustic waves are detected only at the position where the light absorption member 157 is present, the actual detection signal includes a noise component or a false signal as shown in FIG. 5A. The false signal causes artifacts. Referring to FIG. 5A, in particular, a false signal is present in a portion deeper than the distal end portion of the insertion needle 15 of the photoacoustic image.

Referring to FIG. 5B, a noise component is remove by performing smoothing processing on the photoacoustic image shown in FIG. 5A. When a binary image, in which a pixel whose signal strength of the photoacoustic signal is equal to or greater than a threshold value is expressed in white and a pixel whose signal strength of the photoacoustic signal is smaller than the threshold value is expressed in black, is generated by performing binarization processing on the photoacoustic image after the smoothing processing shown in FIG. 5B, the image shown in FIG. 5C is obtained. From such a binary image, a region where white pixels are continuous is extracted as a distal end candidate region from the shallow side of the image. In FIG. 5C, regions 201, 202, and 203 are extracted as distal end candidates.

When a region other than the extracted distal end candidate regions in the photoacoustic image after the smoothing processing shown in FIG. 5B is masked, the image shown in FIG. 5D is obtained. For example, the image shown in FIG. 5D is displayed on the image display means 14. By displaying only a portion corresponding to the distal end candidate region in the photoacoustic image on the image display means 14, extra information is deleted from the photoacoustic image. Accordingly, the doctor or the like can check the position of the insertion needle 15 without being confused by artifacts.

Here, in a case where the light absorption member 157 (refer to FIG. 2) is provided in the insertion needle 15 and light is emitted to the light absorption member 157 to generate photoacoustic waves, the photoacoustic wave generation source is only at the position where the light absorption member 157 is present. In practice, however, since light artifacts or sound artifacts are caused, a photoacoustic image is generated as if photoacoustic waves have been detected from a plurality of positions.

The present inventors have ascertained that all artifacts appear at deeper positions than the actual photoacoustic wave generation source, and have thought that it is necessary to extract a distal end candidate region from the shallow side of the image in order to suppress artifacts. In the present embodiment, the distal end candidate extraction means 29 extracts a distal end candidate region from the shallow side of the photoacoustic image based on the pixel value of the photoacoustic image. By displaying the extracted distal end candidate region, artifacts are suppressed. Therefore, it becomes easy to check the position of the insertion needle 15.

In particular, by setting the upper limit of the number of distal end candidate regions to be extracted and extracting the distal end candidate regions from the shallow side with a predetermined number as an upper limit, artifacts at deep positions are hardly extracted as distal end candidate regions. By suppressing the display of artifacts at deep positions, it becomes easy to check the position of the insertion needle 15.

Figure 6:
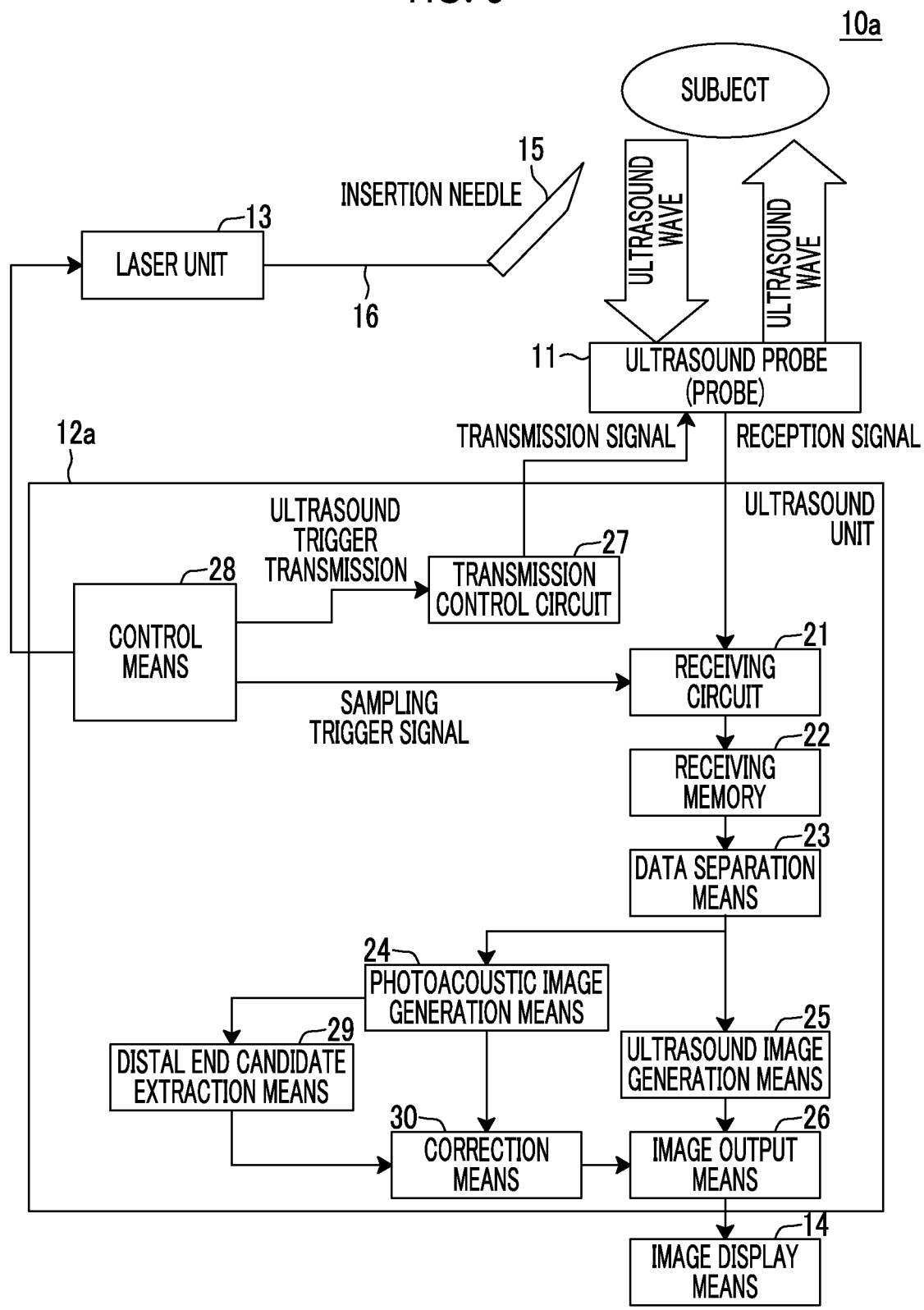
FIG. 6 is a block diagram showing a photoacoustic image generation apparatus according to a second embodiment of the present invention.

Next, a second embodiment of the present invention will be described. FIG. 6 shows the photoacoustic image generation apparatus according to the second embodiment of the present invention. A photoacoustic image generation apparatus 10a according to the present embodiment is different from the photoacoustic image generation apparatus 10 according to the first embodiment shown in FIG. 1 in that a correction means 30 is added to an ultrasound unit 12a. Others may be the same as in the first embodiment.

The correction means 30 receives information regarding the extracted distal end candidate region from the distal end candidate extraction means 29. The correction means 30 corrects the photoacoustic image based on the received information. More specifically, a distal end candidate region other than a distal end candidate region located in the shallowest portion in the photoacoustic image is suppressed relative to the distal end candidate region located in the shallowest portion. The correction means 30 may correct a photoacoustic image for display generated by the photoacoustic image generation means 24, or may correct a photoacoustic signal in the photoacoustic image generation step, specifically, a photoacoustic signal after reconstruction or a photoacoustic signal after detection and logarithmic conversion.

For example, for a distal end candidate region excluding a distal end candidate region located in the shallowest portion among the extracted distal end candidate regions, the correction means 30 corrects the pixel value in each distal end candidate region using a coefficient corresponding to the depth direction between the distal end candidate region excluding the distal end candidate region located in the shallowest portion and the distal end candidate region located in the shallowest portion. The coefficient used for correction is the maximum when the distance is 0, and the value decreases as the distance increases. By the multiplication of such a coefficient, the distal end candidate region located in the shallowest portion in the photoacoustic image can be emphasized relative to the remaining distal end candidate regions.

Figure 7:
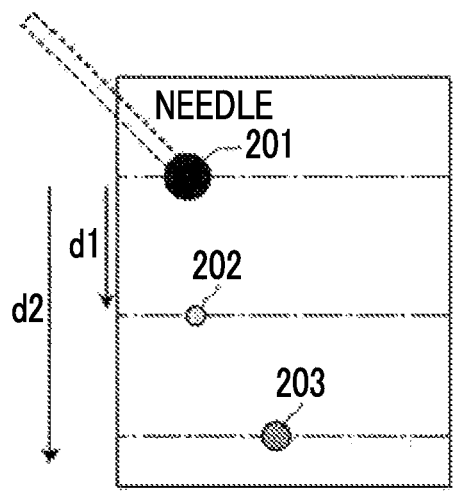
FIG. 7 is a diagram schematically showing a distal end candidate region.

FIG. 7 schematically shows the distal end candidate region shown in FIG. 5C. In FIG. 5C, among the extracted three distal end candidate regions, the distal end candidate region 201 is present at the shallowest position. The correction means 30 calculates a distance in the depth direction between the remaining distal end candidate regions 202 and 203 with the distal end candidate region 201 as a reference. Referring to FIG. 7, the distance in the depth direction between the distal end candidate regions 201 and 202 is d1, and the distance in the depth direction between the distal end candidate regions 201 and 203 is d2. The distance between distal end candidate regions can be defined as a distance between the center-of-gravity positions of respective regions.

Figure 8:
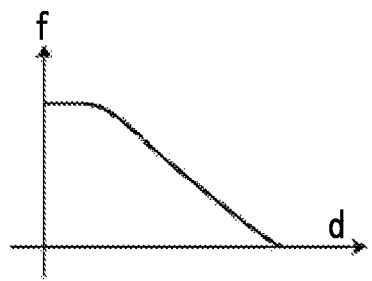
FIG. 8 is a graph showing a specific example of a coefficient.

FIG. 8 shows a specific example of a coefficient. The horizontal axis of the graph shown in FIG. 8 is a distance in the depth direction, and the vertical axis is a coefficient. The coefficient is a function of a distance d, and is expressed as f(d). The coefficient f(d) is a function that monotonically decreases with the distance d. f(d) is the maximum when the distance d is 0, and the value decreases as the distance d increases from the point where the distance d has increased to some extent. For example, when the distance d is 1 cm, the value of f(d) may be about half of the maximum value. f(d) may decrease linearly with respect to the distance d, or may decrease quadratically. Alternatively, f(d) may decrease stepwise.

Figure 9:
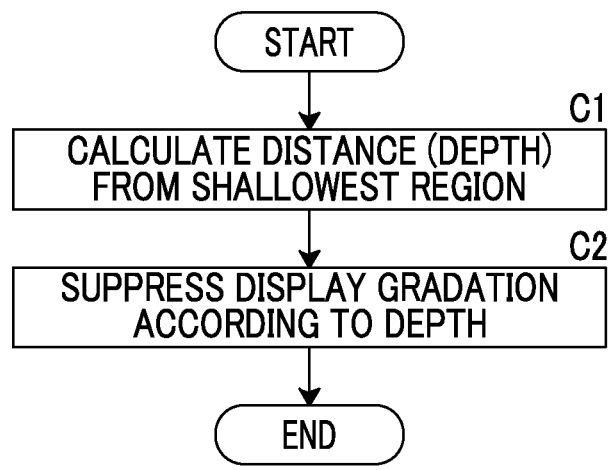
FIG. 9 is a flowchart showing the procedure of correction of a pixel value according to the depth.

FIG. 9 shows a procedure for correcting the pixel value according to the depth. The process shown in FIG. 9 is performed after step A8 in FIG. 3. The correction means 30 calculates a distance in the depth direction between a distal end candidate region located in the shallowest portion, among the distal end candidate regions extracted by the distal end candidate extraction means 29, and each of the remaining distal end candidate regions (step C1). In step C1, for example, a distance d1 between the distal end candidate regions 201 and 202 shown in FIG. 7 and a distance d2 between the distal end candidate regions 201 and 203 are calculated. The correction means 30 suppresses the pixel value of the distal end candidate region according to the depth calculated in step C1 (step C2).

For example, it is assumed that the correction means 30 corrects a photoacoustic signal after detection and logarithmic conversion. A photoacoustic signal of a pixel belonging to the distal end candidate region 201 is set to $I_N$, a photoacoustic signal of a pixel belonging to the distal end candidate region 202 is set to $I_{A1}$, and a photoacoustic signal of a pixel belonging to the distal end candidate region 203 is set to $I_{A2}$. In this case, for the distal end candidate region 201, the correction means 30 leaves the photoacoustic signal $I_N$ as it is without correcting the photoacoustic signal $I_N$. For the distal end candidate region 202, the correction means 30 multiplies the photoacoustic signal $I_{A1}$ corresponding to the depth by the coefficient f(d1), thereby correcting the photoacoustic signal $I_{A1}$ to f(d1)×$I_{A1}$. For the distal end candidate region 203, the correction means 30 multiplies the photoacoustic signal $I_{A2}$ corresponding to the depth by the coefficient f(d2), thereby correcting the photoacoustic signal $I_{A2}$ to f(d2)×$I_{A2}$. The photoacoustic signal after correction is returned to the photoacoustic image generation means 24, and is converted into display gradation using a lookup table or the like.

Figure 10A:
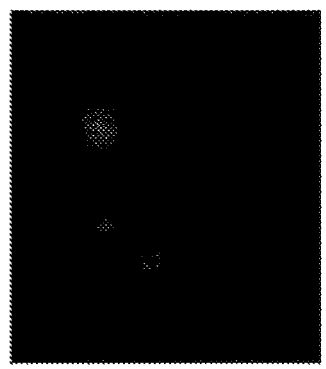
FIG. 10A is a diagram showing a photoacoustic image after correction.
Figure 10B:
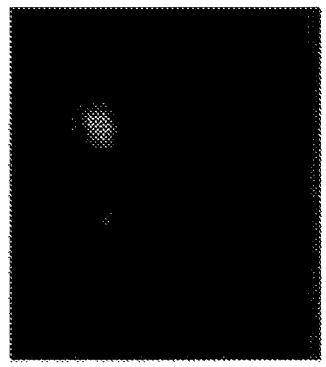
FIG. 10B is a diagram showing a photoacoustic image after correction.

FIGS. 10A and 10B show photoacoustic images after correction. FIG. 10A shows the photoacoustic signal corrected by the correction means 30 as an image, and FIG. 10B shows a photoacoustic image obtained by converting the corrected photoacoustic signal into display gradation. Since the coefficient f(d) is a monotonically decreasing function, the distal end candidate region at a deeper position is suppressed. Accordingly, the distal end candidate region located in the shallowest portion is relatively emphasized. By suppressing the pixel value (signal strength) according to the depth by the correction means 30, artifacts are suppressed as shown in FIGS. 10A and 10B, compared with the image before correction (refer to FIG. 5D). In particular, in FIG. 10B, in the image converted into display gradation using a lookup table or the like, artifacts are almost invisible.

In the present embodiment, the pixel value of each distal end candidate region other than the distal end candidate region located in the shallowest portion, among the extracted distal end candidate regions, is suppressed according to the depth by the correction means 30. In a case where the light absorption member 157 (refer to FIG. 2) is provided in the insertion needle 15 and light is emitted to the light absorption member 157 to generate photoacoustic waves, artifacts appear at a position deeper than the light absorption member 157. In the photoacoustic image, the distal end candidate region located in the shallowest portion is thought to correspond to a region where photoacoustic waves are generated in the light absorption member 157, and a distal end candidate region located in a portion deeper than that is thought to be an artifact. Specifically, it becomes easy to check the position of the insertion needle 15 by relatively emphasizing the distal end candidate region located in the shallowest portion. Even if there is a portion where the photoacoustic signal is strong in a region shallower than a region where photoacoustic waves are generated in the light absorption member 157, it is thought that the distance in the depth direction between the portion and the region where photoacoustic waves are generated in the light absorption member 157 is not large. Accordingly, it is thought that the region where photoacoustic waves are generated in the light absorption member 157 will not be invisible in the photoacoustic image.

In addition, in each of the embodiments described above, the distal end candidate extraction means 29 extracts a distal end candidate region based on the pixel value of the photoacoustic image (signal strength of the photoacoustic signal). However, the distal end candidate extraction means 29 may extract a distal end candidate region based not only on the pixel value but also on the area of a region having a pixel value equal to or greater than the threshold value. For example, a function having a pixel value and the area of a region, in which the pixel value is equal to or greater than the threshold value, as variables may be prepared as an evaluation function indicating the likelihood of the distal end of the insertion needle, and a distal end candidate region may be extracted using the evaluation function. The evaluation function indicates a larger value as the pixel value of a region becomes higher and the area of the region becomes larger, and indicates a smaller value as the pixel value of a region becomes lower and the area of the region becomes smaller, for example. In this case, the distal end candidate extraction means 29 may extract a region having an evaluation value equal to or greater than the threshold value as a distal end candidate region.

Figure 11:
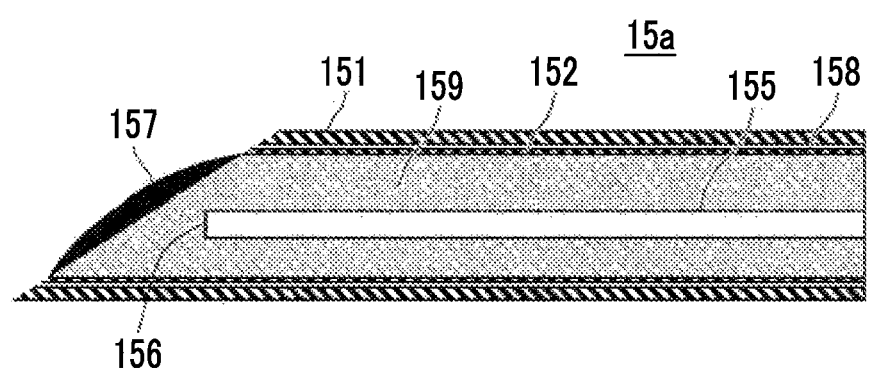
FIG. 11 is a cross-sectional view showing the vicinity of the distal end of an insertion needle in a modification example.

The insertion needle is not limited to that shown in FIG. 2 as long as photoacoustic waves can be generated by light guided to the insertion needle. FIG. 11 shows a cross section of the vicinity of the distal end of an insertion needle in a modification example. An insertion needle 15a in this modification example has an insertion needle body 151 forming the outer needle and an inner needle 152 inserted into the insertion needle body 151. The inner needle 152 includes a light guide member 155, a light absorption member 157, a tube 158, and a transparent resin 159. The tube 158 is a hollow tube formed of polyimide, for example. The tube 158 may be a metal tube formed of stainless steel. The outer diameter of the tube 158 is slightly smaller than the diameter of the inner cavity of the insertion needle body 151. The transparent resin 159 is disposed within the tube 158. For example, an epoxy resin (adhesive) is used as the transparent resin 159. The tube 158 and the transparent resin 159 are cut at an acute angle similar to the insertion needle tip formed at an acute angle. The transparent resin 159 may clog at least a distal end portion of the tube 158, and does not necessarily need to clog the entire inside of the tube 158. As the transparent resin 159, a photocurable resin, a thermally curable resin, or a room temperature curable resin can be used.

Light guided by the optical fiber 16 (refer to FIG. 1) is incident on the light guide member 155 in the inner needle 152 from the optical connector provided in the proximal end portion of the inner needle, for example. Instead of providing the optical connector in the proximal end portion of the inner needle, the optical fiber 16 may be inserted into the tube 158 and the optical fiber 16 itself may be used as the light guide member 155. The light guide member 155 guides the light emitted from the laser unit 13 in the vicinity of the opening of the insertion needle. The light guided by the light guide member 155 is emitted from a light emitting portion 156 provided in the vicinity of the opening. The light guide member 155 is formed of, for example, an optical fiber, and the end surface of the optical fiber on the light traveling side when viewed from the laser unit 13 forms the light emitting portion 156. For example, laser light of 0.2 mJ is emitted from the light emitting portion 156.

The light guide member 155 is embedded into the tube 158 by the transparent resin 159. The light absorption member 157 that is a photoacoustic wave generating portion is disposed at the distal end of the tube 158, and the light emitted from the light emitting portion 156 is emitted to the light absorption member 157. Due to the absorption of the emitted light by the light absorption member 157, photoacoustic waves are generated at the distal end of the insertion needle. Since the light absorption member 157 is present at the distal end of the insertion needle 15a, it is possible to generate photoacoustic waves at one point of the distal end of the insertion needle 15a. Since the length of a photoacoustic wave generation source (sound source) is sufficiently shorter than the length of the entire insertion needle, the sound source can be regarded as a point source. As the light absorption member 157, for example, an epoxy resin containing black pigment mixed thereinto, a polyurethane resin, a fluorine resin, or silicone rubber can be used. Alternatively, a metal or oxide having a light absorption property with respect to the wavelength of laser light may be used as the light absorption member 157. For example, oxides, such as an iron oxide, a chromium oxide, and a manganese oxide having a high light absorption property with respect to the wavelength of laser light, can be used as the light absorption member 157. Alternatively, a metal, such as Ti or Pt, may be used as the light absorption member 157.

The inner needle 152 can be manufactured in the following procedure. First, the transparent resin 159 before curing is injected into the tube 158. Then, the light guide member 155 is inserted into the tube 158, and is positioned such that the light emitting end of the light guide member 155 forming the light emitting portion 156 is disposed in the vicinity of the tube 158. In this positioning, the position may be adjusted such that the light emitting end is disposed at the distal end of the tube 158 by observing the light guide member 155 using a microscope, for example. Here, "vicinity" refers to a position where it is possible to generate photoacoustic waves capable of imaging the position of the distal end of the insertion needle with accuracy, which is required for insertion work in the light absorption member 157 disposed at the distal end, in a case where the light emitting portion 156 is disposed at the position. For example, "vicinity" is the range of 0 mm to 3 mm toward the proximal end side from the distal end of the insertion needle. Since the transparent resin 159 is transparent, it is possible to check the position of the light emitting end of the light guide member 155 during adjustment. Instead of the above, the light guide member 155 may be inserted first, and the transparent resin 159 may be injected thereafter.

After positioning, the transparent resin 159 is cured by heat curing in a state in which the light guide member 155 has been inserted into the tube 158. Then, the distal ends of the tube 158 and the transparent resin 159 are cut at an acute angle so as to have a shape suitable for the distal end of the insertion needle body 151. Then, the resin having a light absorption property that forms the light absorption member 157 is applied to cover at least a part of the cut surface, and the resin is cured by heat curing, for example.

In the above, the light guide member 155 is inserted into the tube 158 and the position is adjusted, and the transparent resin is cured and is then cut at an acute angle. However, the invention is not limited thereto. The tube may be cut at an acute angle first, the light guide member 155 may be inserted into the tube and the position may be adjusted, and the transparent resin may be cured. In this case, a metal tube formed of stainless steel may be used as the tube.

In the above modification example, the example in which the light guide member 155 is embedded into the tube 158 using the transparent resin 159 and the light absorption member 157 is disposed at the distal end of the transparent resin 159 has been described. However, the present invention is not limited thereto. For example, a film having a light absorption property may be used as the light absorption member 157 to cover the light emitting portion 156, which is the light emitting surface of the light guide member 155, with the film having a light absorption property, and the light guide member 155 may be embedded into the transparent resin. Alternatively, a gap may be provided between the light emitting portion 156 of the light guide member 155 and the light absorption member 157, so that the light emitting portion 156 and the light absorption member 157 face each other with the air layer interposed therebetween.

In the modification example shown in FIG. 11, the example in which the inner needle 152 has the tube 158 has been described. However, the present invention is not limited thereto. For example, an inner needle may be formed of a material having a light absorption property, for example, black resin, and the light guide member 155 may be embedded thereinside. In this case, the inner needle, in particular, the distal end portion of the inner needle also serves as the light absorption member 157 that absorbs light, which is emitted from the light emitting portion 156 of the light guide member 155, to generate an acoustic wave. Instead of embedding the light guide member 155 into the resin, the light guide member 155 having almost the same outer diameter as the inner diameter of the insertion needle body 151 may be used, and the light guide member 155 itself may be used as an inner needle. In this case, a film having a light absorption property, for example, a black fluorine resin may be used as the light absorption member 157, so that at least a part of the light guide member 155 including the light emitting portion 156 is covered by the black fluororesin.

The light absorption member 157 is not essential. For example, the light emitted from the light emitting surface of the light guide member 155 may be emitted to the insertion needle body 151, and photoacoustic waves may be generated from a portion to which the light of the insertion needle body 151 is emitted. In this case, the portion to which the light of the insertion needle body 151 is emitted forms a photoacoustic wave generating portion. For example, photoacoustic waves may be generated in the vicinity of the distal end of the insertion needle by emitting light to the inner wall in the vicinity of the distal end of the insertion needle body 151.

The insertion needle is not limited to being percutaneously inserted into the subject from the outside of the subject, and a needle for ultrasound endoscope may be used. The light guide member 155 and the light absorption member 157 may be provided in the needle for ultrasound endoscope, light may be emitted to the light absorption member 157 provided in the distal end portion of the needle, and photoacoustic waves may be detected to generate a photoacoustic image. In this case, it is possible to insert the needle for ultrasound endoscope while checking the position of the distal end portion of the needle for ultrasound endoscope by observing the photoacoustic image. The photoacoustic wave generated in the distal end portion of the needle for ultrasound endoscope may be detected using a probe for body surface, or may be detected using a probe built into the endoscope.

In the embodiment described above, the insertion needle 15 has been considered as an insert. However, the insertion needle 15 is not limited thereto. The insert may be a needle for radiofrequency ablation in which an electrode used in radiofrequency ablation is housed, or may be a catheter inserted into the blood vessel, or may be a guidewire of the catheter inserted into the blood vessel. Alternatively, the insert may be an optical fiber for laser treatment.

Although the needle having an opening at the distal end is assumed as a needle in each embodiment described above, the opening does not necessarily need to be provided in the distal end portion. The needle is not limited to a needle, such as an injection needle, and may be a biopsy needle used for a biopsy. That is, a biopsy needle that can be inserted into the inspection target of the body in order to sample the tissue in the inspection target may be used. In this case, photoacoustic waves may be generated in a sampling portion (inlet port) for sampling the tissue of a biopsy part by sucking the tissue.

In FIG. 1, only one insertion needle 15 is drawn. However, the number of inserts to be imaged in a photoacoustic image is not limited to one. A plurality of sets of inserts and laser units corresponding thereto may be prepared, and a photoacoustic image may be generated for each insert so that the position of each insert can be checked through the photoacoustic image. During image display, the color of a photoacoustic image may be changed for each insert, and the photoacoustic image with the changed color may be superimposed on the ultrasound image. In this case, it is possible to distinguish between a plurality of inserts in the image.

Figure 12:
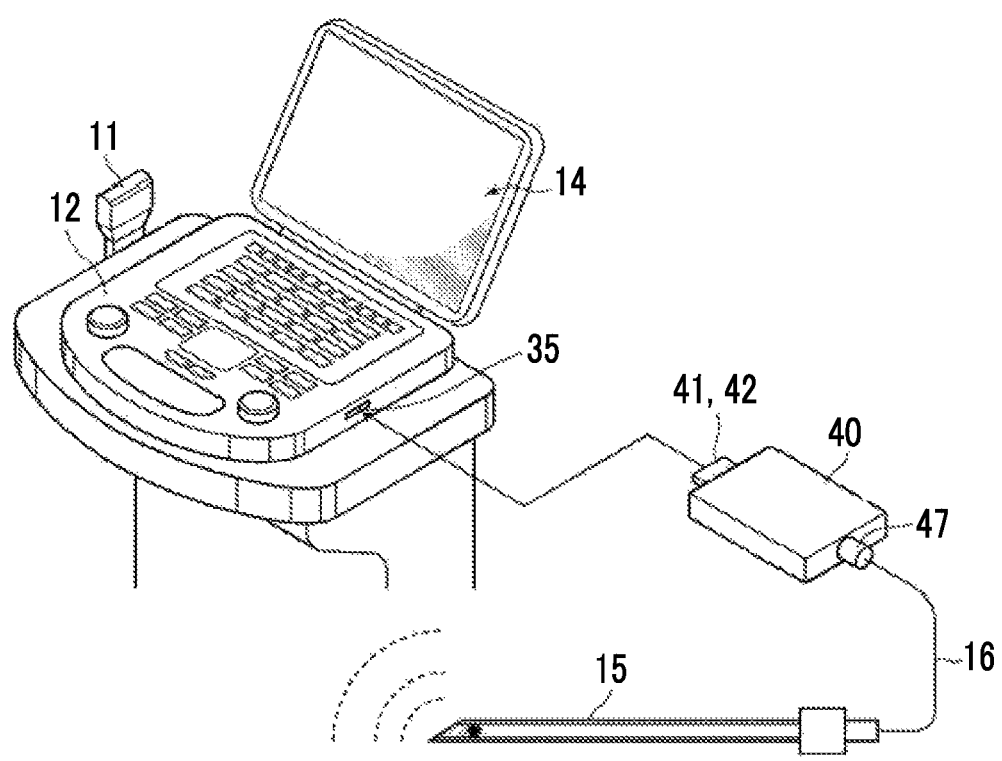
FIG. 12 is a diagram showing the appearance of a photoacoustic image generation apparatus.

Finally, FIG. 12 shows the appearance of a photoacoustic image generation apparatus. The probe 11 is connected to the ultrasound unit 12. The ultrasound unit 12 is configured as an integrated device including the image display means 14. The ultrasound unit 12 typically has a processor, a memory, a bus, and the like. A program regarding photoacoustic image generation is installed in the ultrasound unit 12.

The ultrasound unit 12 has a USB port 40. A USB connector including a power input terminal 41 and a trigger input terminal 42 of a laser unit 13 is inserted into the USB port 40. In a case where the laser unit 13 is a card-sized small and lightweight device, it is possible to hold the USB connector by inserting the USB connector into the USB port of the ultrasound unit 12. The USB port 40 may have any shape allowing a normal USB connector to be inserted thereinto, and does not need to be a port for transmitting and receiving a signal conforming to the normal USB standard. In the USB port, a signal line for a trigger signal may be included instead of a digital signal line. That is, the USB port 40 may be a USB type port as a connector having a total of four terminals of two lines for power supply and two lines for triggering. By using the signal line for a trigger signal instead of the digital signal line, it becomes easy to take trigger synchronization with the laser unit 13.

One end of the optical fiber that forms the light guide member 155 (refer to FIG. 2) of the insertion needle 15 is connected to a light output terminal 47 of the laser unit 13. The optical fiber is inserted into the light output terminal 47, and is held by spring force or the like. If the operator applies a strong force to the light output terminal 47, for example, by pulling the insertion needle 15, the optical fiber exits from the light output terminal 47. Accordingly, it is possible to prevent the optical fiber from being broken. In addition, by making it possible to directly insert or remove the optical fiber into or from the light output terminal 47, there is an effect that the cost can be reduced without providing a connector in the optical fiber extending from the insertion needle 15.

Pulse energy of the pulsed laser light output from the laser unit 13 can be set to 6.4 µJ if the core diameter of the optical fiber forming the light guide member 155 is 200 µm. The pulse energy of the pulsed laser light can be set to 2.0 µJ if the core diameter of the optical fiber is 100 µm. The pulse time width can be set to 80 ns.

In FIG. 12, the light output terminal 47 is provided on a surface opposite to a surface on which the USB connector including the power input terminal 41 and the trigger input terminal 42 is present. However, it is preferable that the light output terminal 47 is provided on a surface perpendicular to the surface on which the USB connector is present. In a case where the USB connector and the light output terminal 47 are provided on the opposite surfaces, if the laser unit 13 is pulled when the operator moves the insertion needle 15, the USB connector may exit from the USB port 40. In contrast, in a case where the USB connector and the light output terminal 47 are provided on the surfaces perpendicular to each other, the USB connector is difficult to exit from the USB port 40 even if the laser unit 13 is pulled.

In FIG. 12, the laser unit 13 is directly connected to the USB port 40. However, the present invention is not limited thereto, and the USB port 40 and the laser unit 13 may be connected to each other using an extension cable or the like. The trigger input terminal 42 does not need to be included in the USB connector, and the laser unit 13 may acquire a trigger signal from a connector (terminal) different from the USB port 40. For example, a trigger signal may be acquired from a connector for electrocardiogram (ECG) measurement attached to the normal ultrasound system. Alternatively, a trigger signal may be acquired from some terminals of the connector of the probe.

While the present invention has been described based on the preferred embodiment, the photoacoustic image generation apparatus is not limited only to the above embodiments, and various modifications and changes in the configuration of the above embodiment are also included in the range of the present invention.

What is claimed is:

1. A photoacoustic image generation apparatus, comprising:
   an insert at least a part of which is inserted into a subject and which has a light guide member for guiding light emitted from a light source, a light emitting portion for emitting light guided by the light guide member, and a photoacoustic wave generating portion for generating photoacoustic waves caused by light emitted from the light emitting portion;
   an acoustic wave detector including a probe for detecting photoacoustic waves emitted from the insert; and
   a controller configured to:
      generate a photoacoustic image based on a detection signal of the photoacoustic waves;
      extract a distal end candidate region from a shallow side based on a strength of the detection signal of the photoacoustic waves; and
      display the distal end candidate region that was extracted on image display.

2. The photoacoustic image generation apparatus according to claim 1,
   wherein the controller extracts a distal end candidate region based on the strength of the detection signal.

3. The photoacoustic image generation apparatus according to claim 1, the controller further configured to:
   when a plurality of the distal end candidate regions are extracted, suppressing a strength of a detection signal of photoacoustic waves in a distal end candidate region other than a distal end candidate region located in a shallowest portion in the photoacoustic image when imaging is realized, among the plurality of extracted distal end candidate regions, relative to a strength of a detection signal of photoacoustic waves in the distal end candidate region located in the shallowest portion.

4. The photoacoustic image generation apparatus according to claim 3,
   wherein, with the distal end candidate region located in the shallowest portion among the extracted distal end candidate regions as a reference, the controller corrects a strength of a detection signal of photoacoustic waves in each distal end candidate region using a coefficient according to a distance in a depth direction between each distal end candidate region and the reference distal end candidate region.

5. The photoacoustic image generation apparatus according to claim 4,
   wherein the controller emphasizes the distal end candidate region located in the shallowest portion relative to remaining distal end candidate regions.

6. The photoacoustic image generation apparatus according to claim 4,
   wherein the distance is defined as a distance in the depth direction between a center-of-gravity position of the reference distal end candidate region and each of remaining distal end candidate regions.

7. The photoacoustic image generation apparatus according to claim 4,
   wherein the coefficient is a maximum when the distance is 0, and a value of the coefficient decreases as the distance increases.

8. The photoacoustic image generation apparatus according to claim 1,
   wherein the controller extracts, as a distal end candidate region, a region based on the strength of the detection signal of the photoacoustic waves.

9. The photoacoustic image generation apparatus according to claim 1,
   wherein the controller extracts a distal end candidate region based not only on the strength of the detection signal of the photoacoustic waves but also on an area of a region that is determined based on the strength of the detection signal of the photoacoustic waves.

10. The photoacoustic image generation apparatus according to claim 1,
    wherein the controller masks a region other than the extracted distal end candidate region in the photoacoustic image.

11. The photoacoustic image generation apparatus according to claim 1,
    wherein the controller extracts the distal end candidate region after performing smoothing processing on the detection signal of the photoacoustic waves.

12. The photoacoustic image generation apparatus according to claim 1,
    wherein the insert has an opening, and has an inner cavity thereinside.

13. The photoacoustic image generation apparatus according to claim 12,
    wherein the light emitting portion emits light beams guided by the light guide member toward an inner wall of the inner cavity.

14. The photoacoustic image generation apparatus according to claim 1,
    wherein the photoacoustic wave generating portion includes a light absorption member that absorbs the light emitted from the light emitting portion to generate photoacoustic waves.

15. The photoacoustic image generation apparatus according to claim 1,
    wherein the insert is a needle inserted into a subject.

16. The photoacoustic image generation apparatus according to claim 1,
    wherein the acoustic wave detector further detects reflected acoustic waves of acoustic waves transmitted toward a subject, and
    the controller is further configured to generate a reflected acoustic wave image based on the reflected acoustic waves is further provided.

17. The photoacoustic image generation apparatus according to claim 16,
wherein the controller displays the distal end candidate region that was extracted on the image display so as to be superimposed on the reflected acoustic wave image.

\* \* \* \* \*